United States Patent
Berube et al.

(10) Patent No.: US 9,746,120 B2
(45) Date of Patent: Aug. 29, 2017

(54) APPARATUS FOR CLOSING AND SEALING THE OPEN END OF A PIPE

(71) Applicant: Car-Ber Investments Inc., Wallaceburg (CA)

(72) Inventors: Guy Berube, Sarnia (CA); Tom Blair, Port Lambton (CA); Dave Uzonyi, Wallaceburg (CA)

(73) Assignee: CAR-BER Investments Inc., Wallaceburg (CA)

( * ) Notice: Subject to any disclaimer, the term of this patent is extended or adjusted under 35 U.S.C. 154(b) by 193 days.

(21) Appl. No.: 14/765,415

(22) PCT Filed: Feb. 3, 2014

(86) PCT No.: PCT/CA2014/000079
§ 371 (c)(1),
(2) Date: Aug. 3, 2015

(87) PCT Pub. No.: WO2014/117262
PCT Pub. Date: Aug. 7, 2014

(65) Prior Publication Data
US 2015/0362114 A1      Dec. 17, 2015

Related U.S. Application Data

(60) Provisional application No. 61/760,515, filed on Feb. 4, 2013.

(51) Int. Cl.
*F16L 55/10*        (2006.01)
*F16L 55/115*       (2006.01)
(Continued)

(52) U.S. Cl.
CPC ....... *F16L 55/1152* (2013.01); *F16L 55/1108* (2013.01); *F16L 55/1286* (2013.01); *G01M 3/022* (2013.01); *G01N 3/12* (2013.01)

(58) Field of Classification Search
CPC .......................... F16L 55/1152; F16L 55/1108
(Continued)

(56) References Cited

U.S. PATENT DOCUMENTS 1,099,158 A    6/1914   Baker
3,765,560 A    10/1973  Kemp
(Continued)

FOREIGN PATENT DOCUMENTS

WO        2011/106893 A1    9/2011

OTHER PUBLICATIONS

International Search Report and Written Opinion of the International Searching Authority dated Apr. 28, 2014, PCT Application No. PCT/CA2014/000079, filed Feb. 3, 2014.

*Primary Examiner* — Vishal Pancholi
(74) *Attorney, Agent, or Firm* — Marsh Fischmann & Breyfogle LLP; Jonathon A. Szumny

(57) ABSTRACT

The tool comprises a front plate for closing the open end of a pipe. A pair of clamping devices are positioned around the pipe and frictionally engage its outer surface. Nut and bolt assemblies connect the front plate with the clamps. These assemblies pull the front plate tight against the pipe end face. A back plate is positioned transversely within the bore of the pipe. The plate has a stem that slidably projects forwardly through a central aperture in the front plate. The back plate carries an O-ring. A nut is threaded onto the stem and functions to draw the back plate forward so that the O-ring seals the interface of the front plate and pipe end face.

2 Claims, 3 Drawing Sheets

(51) Int. Cl.
  *G01N 3/12* (2006.01)
  *G01M 3/02* (2006.01)
  *F16L 55/11* (2006.01)
  *F16L 55/128* (2006.01)

(58) Field of Classification Search
  USPC .................. 138/89.1–89.4, 89, 90, 96 R
  See application file for complete search history.

(56) References Cited

U.S. PATENT DOCUMENTS

| | | | | |
|---|---|---|---|---|
| 5,437,309 A | * | 8/1995 | Timmons | F16L 57/005 138/89 |
| 5,660,293 A | | 8/1997 | Strom | |
| 6,029,709 A | * | 2/2000 | Burgess | F16L 55/11 138/89 |
| 6,463,791 B1 | * | 10/2002 | Berube | G01M 3/2884 73/46 |
| 6,883,546 B1 | * | 4/2005 | Kobylinski | F16L 55/132 138/89 |
| 7,669,899 B2 | * | 3/2010 | Carson | F16L 55/11 138/89 |
| 2003/0150500 A1 | * | 8/2003 | Molina | E03D 11/16 138/89 |

* cited by examiner

APPARATUS FOR CLOSING AND SEALING THE OPEN END OF A PIPE

FIELD OF THE INVENTION

The invention relates to a mechanical assembly or tool for use in closing and sealing the open end of a steel pipe which is to undergo hydraulic pressure testing.

BACKGROUND

It is common practice to hydraulically pressure test a joint of steel pipe to assess its integrity. For example this is done in manufacturing yards where piping, valves, vessels, instruments and the like are connected together into modular assemblies.

The pressure test is commonly conducted at high pressure (as much as 5,000 psi). So the assemblies closing the open ends of a joint undergoing testing need to be competent to remain in place and leak-proof.

One suitable tool for this purpose is disclosed in our PCT publication WO2011/106893 A1. In FIGS. 10-15 this publication shows:

- an external front plate which functions to abut the end face of a pipe end to close its bore opening;
- an external circumferential clamp assembly which tightens onto and frictionally engages or grips the outer surface of the pipe end and anchors the assembly in place;
- threaded nut and bolt means extending between the plate and clamp for drawing the plate tightly against the pipe end face; and
- annular seal means interposed between the plate and pipe end face for sealing their interface.

While the '893 tool has proven commercially viable, there remains a need for an improved tool characterized by: a simpler structure; reduced installation time; minimal internal scoring of the pipe inner surface; concentrated gripping power; and sealing capability which increases as the pressure in the pipe increases.

SUMMARY OF THE INVENTION

In one embodiment, a tool for closing and sealing the open end of a pipe is provided, the tool having front and back ends and comprising, in combination:

- an external front plate for extending across and abutting the open end face of the pipe, to form an annular interface therewith;
- the front plate having a central aperture extending therethrough and a peripheral flange for projecting radially beyond the pipe outer surface;
- an axially movable back plate for transversely positioning within the bore of the pipe, said back plate carrying at its front end an annular, resilient, deformable seal means for sealing the interface;
- the back plate being connected at its front end with a forwardly projecting stem adapted to slidably extend through the aperture, whereby the back plate and stem may move as a unit to deliver the seal means to the interface and compress it there against;
- a first clamp means for positioning around the pipe and means for tightening said clamp means so it may frictionally engage the pipe to anchor the first clamp means in place thereon;
- a second clamp means for positioning adjacent the rear end of the first clamp means, said second clamp means being operative to frictionally engage the pipe upon actuation thereof;
- means for biasing the front plate against the pipe end face and actuating the second clamp means; and
- means for drawing the back plate toward the front plate to thereby bring the seal means into compressed sealing engagement with the front plate and inner surface of the pipe along the length of the interface and for disengagably locking the stem in place.

Preferably, the first clamp means is a split, flanged and threadably bolted together assembly.

Preferably, the second clamp means comprises: a segmental annular gripper having circumferentially spaced apart segments and a rearwardly and downwardly sloped outer surface; and a compression ring, mountable on the gripper and having a forwardly and upwardly sloped inner surface for engaging the gripper sloped outer surface whereby, if the compression ring is urged forwardly, it impels the gripper ring downwardly into tight frictional engagement with the pipe.

Preferably, a set of axially extending threaded bolts connect the front plate and second clamp means and threaded nuts, abutting the front surface of the front plate and the back surface of the second clamp means, may tighten the front plate against the pipe end face and actuate the second clamp means.

Preferably, the back plate is dimensioned to have an annular clearance relative to the inner surface of the pipe.

From the foregoing it will be understood: that increasing pressure within the bore of the pipe will push on the back plate when it presses against the front plate to increase compression and sealing of the seal means; that the slidable back plate preferably has a circumferential clearance with the pipe's inner surface so as to avoid scoring it and the stem functions to centralize the plate; that the first clamp means provides an anchoring function which enables the set of axial bolts and nuts to both draw the front plate into abutment with the end face of the pipe and to pull the compression ring forwardly along the gripper to thereby actuate the second clamp means into frictional engagement with the pipe; and that two distinct clamping actions are implemented within the length of a single set of axial bolts.

In another embodiment, the invention is concerned with a tool for closing and sealing an open end of a pipe, said tool having front and back ends, said pipe having an end face, a bore, an end opening and inner and outer surfaces, said tool comprising, in combination: an external front plate for extending across and abutting the pipe end face to form an annular interface therewith, said front plate having a flange extending beyond the pipe outer surface; said front plate having a central aperture extending through it; a clamp means for extending around, clamping onto and frictionally engaging the pipe outer surface to anchor said clamp means thereto; means, connecting the front plate and clamp means, for drawing the front plate into tight engagement with the pipe end face; a movable back plate for positioning with clearance within the bore of the pipe so as to extend transversely thereof, said back plate carrying an annular, deformable, resilient seal means at its front end for sealing the interface; said back plate further having a forwardly projecting stem for slidably extending through the aperture; said back plate and stem forming a unit which is movable in use so as to deliver the seal means to the interface and compress it against the front plate and pipe inner surface to seal the interface; and disengagable means, mountable on the stem for biasing the unit into sealing position and locking it in said position.

DESCRIPTION OF THE PREFERRED EMBODIMENT

Figure 1:
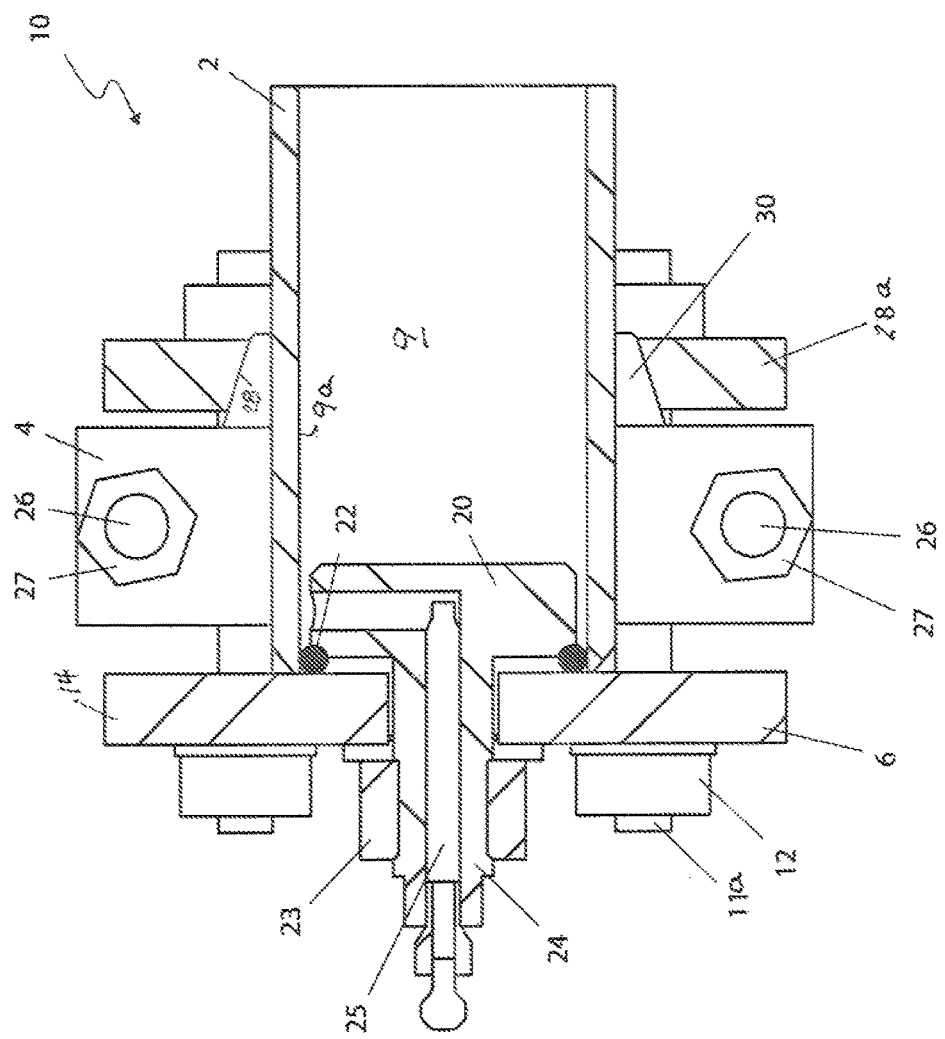
FIG. 1 is a sectional side view of the tool.
Figure 2:
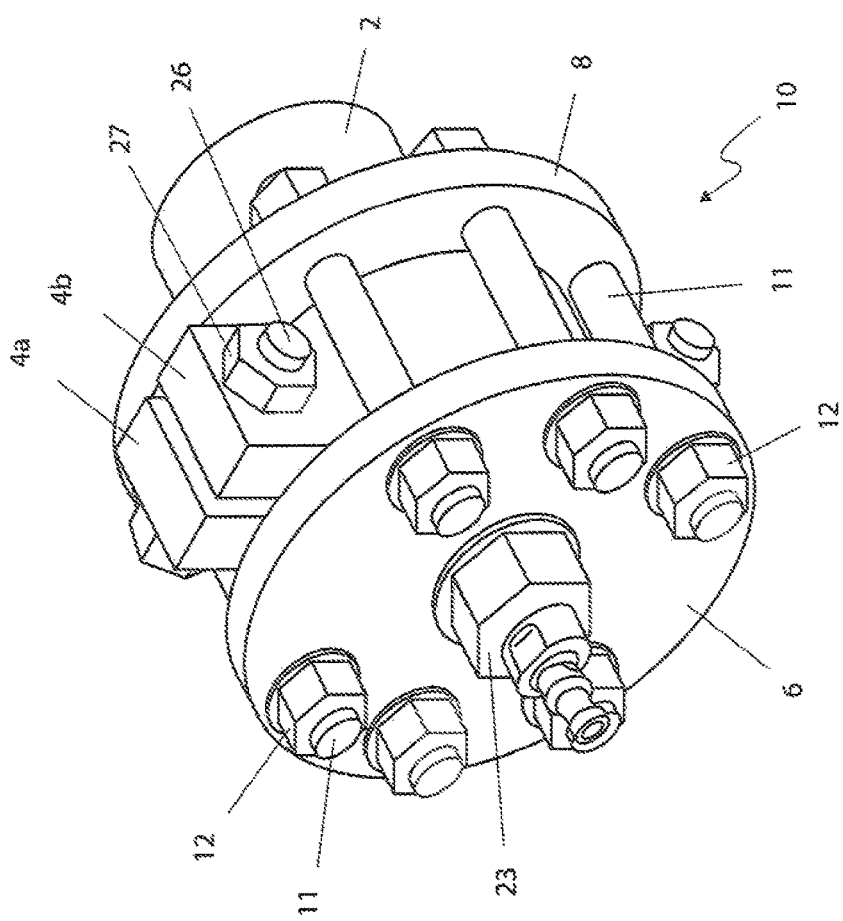
FIG. 2 is a perspective view of the tool of FIG. 1.
Figure 3:
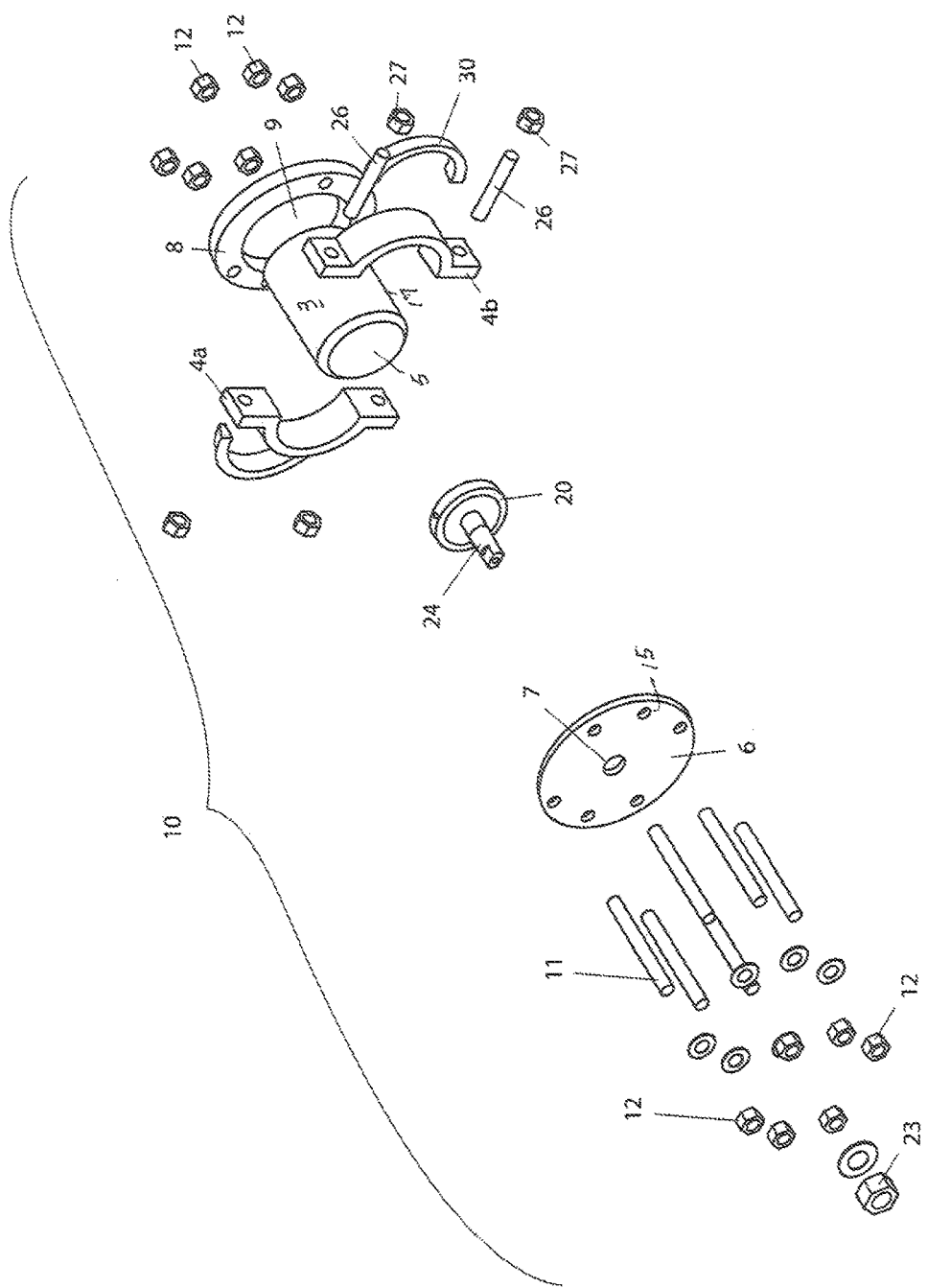
FIG. 3 is an exploded view of the tool.

The invention provides a mechanical assembly or tool 10 for closing and sealing the open end 2 of a pipe 3 which is, for example, to undergo hydraulic pressure testing.

In general outline, the tool 10 comprises: a front plate 6 for closing the opening 5 at the end 2 of the pipe 3; a split, flanged, bolted first clamp 4, comprising sections 4a, 4b, adapted to extend around the pipe 3 and operative, when tightened, to frictionally engage the pipe's outer surface 17 and to provide an anchoring function; a second clamp 8, positioned rearwardly of and abutting the first clamp 4, for also frictionally engaging the pipe's outer surface 17; several axially extending threaded bolt and nut assemblies 11a; each assembly 11a having a bolt 11 extending through and connecting the front plate 6 and first and second clamps 4, 8 and nuts 12 for biasing the front plate 6 into abutting relation with the end face of the pipe 3, to thereby form an interface; the nut and bolt assemblies 11a further function to actuate the second clamp 8, as described below; a movable internal back plate 20 is positioned within the bore 9 of the pipe 3 and is oriented transversely relative to the pipe axis; the front end of the back plate 20 is configured to carry an annular seal 22 for sealing the interface; a stem 24 slidably extends forwardly from the back plate 20 through a central aperture 7 extending axially through the front plate 6; a nut 23 threads on the stem 24 and functions to draw the back plate 20 toward the front plate 6 so that the seal 22 is compressed against the front plate 6 and pipe inner surface 9a so as to seal the interface; and a passageway 25 extends through the stem 24 and back plate 20 for delivery of pressure testing fluid into the bore 9 of the pipe 3.

In greater detail, the tool 10 comprises an externally positioned front plate 6 adapted to extend across and close the pipe opening 5. The diameter of the front plate 6 is greater than that of the pipe 3, so as provide a peripheral outer flange 14. A series of spaced apart bolt holes 15 extend through the flange 14, parallel to the axis of the pipe 3. A central aperture 7 also extends axially through the plate 6.

A split and flanged first clamp 4 is positioned around the pipe 3. The inner diameter of the sections 4a, 4b of the clamp 4 is slightly less than the outer diameter of the pipe 3. Transversely oriented bolt holes extend through the flanges of the sections 4a, 4b. Threaded bolts 26 extend through the flange bolt holes. Nuts 27 are threaded onto the bolts 2b and pull the clamp sections 4a, 4b tightly about the pipe 3 so that they clamp onto and frictionally engage the outer surface of the pipe 3. In sum, the bolted sections 4a, 4b provide a circumferential first clamp 6 anchored on the pipe 3.

A segmental annular gripper ring 30 is mounted about the pipe 3, rearwardly of the first clamp 4. The inner surface of the gripper ring 30 is flat and conforms to the outer surface of the pipe 3. The outer surface 28 of the gripper ring 30 is downwardly sloped to the rear.

A compression ring 28a seats on the gripper ring 30. The inner surface 31 of the compression ring 28a is upwardly sloped to the front and conforms with the gripper ring's outer surface 28. A series of bolt holes 30 extend through the compression ring 28a.

As previously stated, bolts 11 extend axially through the bolt holes of the front plate 6 and compression ring 28a. Nuts 12 are threaded onto the front and back ends of the bolts 11 and function to draw the front plate 6 into abutting relation with the pipe end face and to urge the compression ring 28a into tight engagement with the gripper ring 30, thereby driving the gripper ring downwardly or radially to frictionally engage the pipe 3.

Collectively the gripper ring 30, compression ring 28a and nut and bolt assemblies 11a provide a second clamp 8 which may be actuated to deliver a downwardly directed frictional engagement with the pipe 3.

From the foregoing it will be noted that only two sets of bolts and nuts are used to apply and activate a clamping means, comprising a circumferentially acting first clamp 4 and a radially acting second clamp 8.

A back plate 20 is transversely positioned within the pipe bore 9. The back plate 20 has a clearance with the inner surface 9a of the pipe 3, so that it may move forwardly toward the front plate 6. The front end of the back plate 20 forms an annular seat for receiving and carrying an O-ring seal 22. The seal 22 is resilient and deformable.

A forwardly projecting stem 24 is connected to the front face of the back plate 20. The stem 24 slidably extends through the central aperture 7 of the front plate 6, so that it is externally accessible. The stem and back plate together form a movable back plate unit.

The outer surface of the stem 24 is threaded. A nut 23 is threaded thereon. The nut 23 functions to draw the back plate 20 forwardly toward the front plate 6, to thereby press the O-ring seal 22 against the front plate 6 and pipe inner surface 9a, for sealing the interface. The nut 23 further functions to lock the back plate unit in place.

The stem 24 and back plate 20 may form an internal passageway 25 through which test water may be introduced into the pipe bore 9.

The invention claimed is:

1. A tool for closing and sealing the open end of a pipe, the tool having front and back ends and comprising, in combination:

an external front plate for extending across and abutting the open end face of the pipe, to form an annular interface therewith;

the front plate having a central aperture extending therethrough and a peripheral flange for projecting radially beyond the pipe outer surface;

an axially movable back plate for transversely positioning with clearance within the bore of the pipe, said back plate carrying at its front end an annular, resilient, deformable seal means for sealing the interface by contacting with the front plate and the pipe inner surface;

the back plate being connected at its front end with a forwardly projecting stem adapted to slidably extend through the aperture, whereby the back plate and stem may move as a unit to deliver the seal means to the interface and compress it against the front plate and pipe;

a first clamp means for positioning around the pipe and means for tightening said clamp means so it may frictionally engage the pipe to anchor the first clamp means in place thereon;

a second clamp means for positioning on the pipe at the rear end of the first clamp means, said second clamp means comprising a ramped compression ring mounted on a ramped segmental gripper ring, said second clamp means being operative to frictionally engage the pipe upon actuation thereof;

bolt means for connecting the front plate and compression ring, whereby said bolt means biases the front plate against the pipe end face and actuates the second clamp means by pulling on the compression ring; and means, associated with the stem, for drawing the back plate toward the front plate, to thereby bring the seal means into compressed sealing engagement with the front plate and inner surface of the pipe along the length of the interface, and for disengagably locking the stem in place.

2. The tool of claim 1, wherein the stem forms a passage for extending through the front and back plates for introducing pressure testing fluid into the pipe bore.

* * * * *